(12) United States Patent
DeTore

(10) Patent No.: US 8,457,980 B1
(45) Date of Patent: Jun. 4, 2013

(54) METHOD OF ADMINISTERING THE DELIVERY OF HEALTH CARE SERVICES

(75) Inventor: Arthur W. DeTore, Fort Wayne, IN (US)

(73) Assignee: Parkview Health System, Inc., Fort Wayne, IN (US)

( * ) Notice: Subject to any disclaimer, the term of this patent is extended or adjusted under 35 U.S.C. 154(b) by 2117 days.

(21) Appl. No.: 10/414,853

(22) Filed: Apr. 16, 2003

Related U.S. Application Data

(60) Provisional application No. 60/373,257, filed on Apr. 17, 2002.

(51) Int. Cl.
*G06Q 50/00* (2006.01)
*G06Q 10/00* (2006.01)

(52) U.S. Cl.
USPC .................................................. 705/2; 705/3

(58) Field of Classification Search
USPC ....................................................... 705/4, 2–3
See application file for complete search history.

(56) References Cited

U.S. PATENT DOCUMENTS

| | | | |
|---|---|---|---|
| 4,839,806 A * | 6/1989 | Goldfischer et al. .......... | 700/231 |
| 5,072,383 A * | 12/1991 | Brimm et al. .................... | 705/2 |
| 5,535,322 A * | 7/1996 | Hecht .............................. | 705/1 |
| 5,940,829 A * | 8/1999 | Tsuiki et al. ..................... | 707/10 |
| 6,003,011 A * | 12/1999 | Sarin et al. ........................ | 705/9 |
| 6,714,913 B2 * | 3/2004 | Brandt et al. ..................... | 705/2 |
| 2002/0055868 A1 * | 5/2002 | Dusevic et al. .................. | 705/9 |
| 2002/0099571 A1 * | 7/2002 | Waku et al. ...................... | 705/2 |
| 2003/0050821 A1 * | 3/2003 | Brandt et al. ..................... | 705/9 |

OTHER PUBLICATIONS

Jeffrey Rayport and John J. Sviokla; "Exploiting the Virtual Value Chain;" Harvard Business Review (Nov.-Dec. 1995); reprint 95610; pp. 75-85.

* cited by examiner

*Primary Examiner* — Sheetal R Rangrej
(74) *Attorney, Agent, or Firm* — Barnes & Thornburg LLP

(57) ABSTRACT

A method of administering the delivery of health care services comprises identifying a plurality of patient-centric tasks which form at least a portion of a health care delivery process, classifying the tasks as physical and/or virtual tasks, and mapping a patient-centric workflow which incorporates the tasks. In certain embodiments physician-performed and non-physician-performed tasks are further identified, as are tasks which require the physical presence of both patient and physician or nonphysician at particular locations at particular times. Automated means for facilitating performance of the tasks may also be provided. The method may be applied to an existing health care delivery process, used in the modification of an existing process, or used in the design of a new process.

6 Claims, 11 Drawing Sheets

FIG. 3

Flowchart Key — 32

- 34 All Nurses Physical
- 36 Clerk Physical
- 38 Other Physical
- 40 Other Ancillary Physical

- 42 Physician Physical
- 44 Physician Virtual / All Nurses Virtual / Clerk Virtual / Other Virtual / Other Ancillary Virtual
- 46 Physician Both Physical & Virtual / All Nurses Both Physical & Virtual / Clerk Both Physical & Virtual / Other Both Physical & Virtual / Other Ancillary Both Physical & Virtual

- 50 Indicates an Activity or Document Not Associated with an Individual
- 48 Indicates Decision to be Made

METHOD OF ADMINISTERING THE DELIVERY OF HEALTH CARE SERVICES

RELATED APPLICATIONS

The present application is related to and claims priority to U.S. Provisional Patent Application Ser. No. 60/373,257, filed on Apr. 17, 2002, entitled System and Method for Administering the Delivery of Health Care Services. The subject matter disclosed in that provisional application is hereby expressly incorporated into the present application.

FIELD OF INVENTION

The present invention relates generally to the field of health care and, more particularly, to a method for administering the delivery of services in the health care field.

BACKGROUND

The health care industry is, in many respects, a knowledge-based industry administered by knowledge workers. There is a need to increase the productivity of knowledge work and knowledge workers in the health care industry.

This is more important given today's health care environment than it was several years ago. There are major legislative, as well as economic pressures driving health care to become more productive. Reimbursements from Medicare, Medicaid and private payors are decreasing.

At the same time, the competitive environment for health care companies is very intense. There are pressures for lower costs as well as greater safety and higher quality of care. Some large national employer groups have banded together and developed initiatives to address the issues of quality, safety and cost. Further, there are other groups such as the Institute of Medicine, which are calling for new patient safety standards.

One of the major recommendations for enhanced quality, safety and lower costs is the use of electronic medical records and computer physician order entry (CPOE) to avoid confusion in ordering medications, diagnostic tests and other procedures and treatments. Although hailed as an excellent approach, this has been extremely difficult to implement in practice. It is estimated that today only 3% of physicians practice CPOE and that most of these implementations have been accomplished with residents or in academic settings in which the physicians are hospital employees. CPOE is very difficult and must be done in a way that adds value to physicians or it will be resisted.

The workflow models and processes that have been developed to implement CPOE have assumed that the physician is an integral part of the health care organization's environment and internal workflow. In some settings, this is not the case. Especially in community settings, the physician is an alliance partner in delivering health care and is not an employee. The physician is working more as an independent contractor. As a result, the independent physician is concerned about delivering quality patient care as well as cost effective care, and although s/he is concerned about the overall productivity of the health care organization, s/he is especially concerned about her/his productivity as an individual worker. In the case of the physician alliance partner, the physician must be concerned about her/his workflow and how it interfaces with the workflow of the organization. However, her/his workflow is not an integral component of the overall workflow, unlike the resident physician or physician employee, rather the independent physician spends only a component of her/his time at a given health care organization. Therefore, a different perspective is necessary.

To successfully implement CPOE and enhance productivity, health care organizations must focus on how to decrease transaction costs in the organization, that is, the costs of searching for, negotiating for, contracting for and administering resources and information. Also, health care organizations must achieve this with a patient-centric, quality focus while not alienating or decreasing the productivity of the major knowledge worker, the physician who is an alliance partner and not an employee.

One framework which accomplishes this is the concept of the "Virtual Value Chain," a concept discussed by Jeffery Rayport and John Sviokla in their 1995 *Harvard Business Review* article, "Exploiting the Virtual Value Chain." The article differentiates the "physical world of resources" from the "virtual world of information" and compares and contrasts the physical value chain of the organization, which delivers the organization's products or services with its virtual value chain, which is the information flow of the organization. It states, "Executives must pay attention to how their companies create value in both the physical world and the virtual world."

In the physical world of health care, health care organizations must focus on "re-engineering" their processes and workflows to be patient-centric and quality-based. However, the virtual value chain should focus on creating value for all knowledge workers, especially physicians, enhancing productivity by decreasing transaction costs and enhancing quality with better decisions.

SUMMARY

One aspect of the current invention relates to automation of the information flow of health care organizations to provide higher quality of care and patient safety through improved patient-centric workflow, better decision making and reduction of administrative errors.

Another aspect of the invention relates to enhancement of the productivity of physicians through automation of workflows, including physician computer order entry.

These and other aspects are achieved in a method of administering the delivery of health care services, comprising the steps of: identifying a plurality of patient-centric tasks which form at least a portion of a health care delivery process; classifying the tasks identified as a physical task, a virtual task, or a combined physical/virtual task; and mapping the tasks to produce a process flow which incorporates the tasks. In one embodiment, the method further comprises the additional step of identifying, from within the plurality of patient-centric tasks, at least one physician-performed task. This embodiment further comprises the step of classifying the physician-performed task as a physical task, a virtual task or a combined physical/virtual task. One embodiment further comprises the step of identifying one or more of the physician-performed tasks that require the presence of both patient and physician.

Certain embodiments of the present method may comprise the step of providing means for remotely performing a plurality of the physician-performed tasks classified as virtual or combined physical/virtual tasks. This and other embodiments may further comprise the step of providing automated means for facilitating at least one of the physician performed tasks relating to data gathering, decision making, distributing resources, educating, doing or documenting.

One or more embodiments of the present method may comprise the step of identifying functional areas of one or more health care organizations responsible for at least one of the plurality of tasks. In this and other embodiments, the mapping step comprises the step of creating a flow diagram for at least a portion of the health care delivery process, and identifying at least a portion of a plurality of tasks defined in the flow diagram as a physical task, a virtual task or a combined physical/virtual task.

The method of the present invention may be used with an existing heath care delivery process. In this instance, the method may comprise the step of redesigning the existing process to include an alternative set of patient-centric tasks, whereby said process is changed by changing the number of the plurality of tasks or by changing the number of virtual tasks. Alternatively, the method may also be used with a new health care delivery process. In that case, the method may further comprise the step of designing the new process to include a plurality of patient-centric tasks, including a plurality of virtual tasks.

The present method may further comprise the additional step of identifying, from within the plurality of patient-centric tasks, at least one nonphysician-performed task. This embodiment may further comprise the additional step of classifying the nonphysician-performed task as a physical task, a virtual task or a combined physical/virtual task. Certain embodiments may include the additional step of identifying the patient-centric tasks and the nonphysician-performed tasks that require the presence of both patient and nonphysician. The additional step of providing means for remotely performing a plurality of the nonphysician-performed tasks classified as virtual or combined physical/virtual tasks may also be performed. This and other embodiments may further comprise the additional step of providing automated means for facilitating at least one of a nonphysician performed task relating to data gathering, decision making, distributing resources, educating, doing or documenting.

Additional embodiments, features and advantages will become apparent to those skilled in the art upon consideration of the following description of the illustrated embodiment exemplifying the best mode of carrying out the invention.

BRIEF DESCRIPTION OF THE DRAWINGS

FIG. 3 is a flowchart key used in connection with interpreting the flowcharts of the other figures.

FIG. 4b is a continuation of the flowchart of FIG. 4a.

FIG. 5b is a continuation of the flowchart of FIG. 5a.

DETAILED DESCRIPTION

Figure 1:
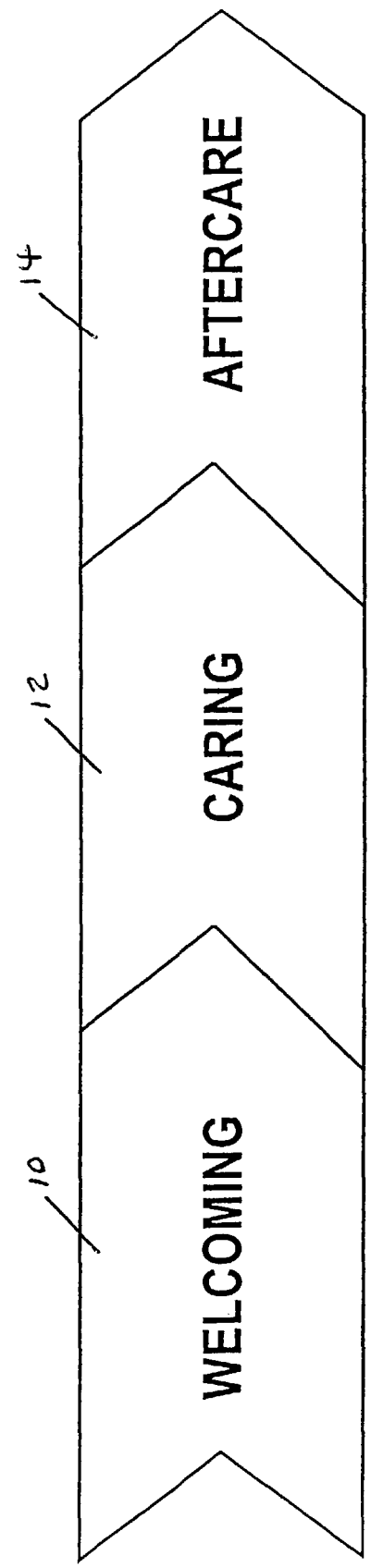
FIG. 1 is a diagram representing a patient-centric workflow.

FIG. 1 is a diagram representing a patient-centric workflow. The physical workflow of a health care organization should be focused on the patient. In many organizations, focusing on patient-centric workflows may be considered a non-traditional approach, since most health care organizations are organized in departments such as admitting, x-ray, nursing, etc. A patient is moved through the various departments during their ambulatory visit or inpatient stay to receive needed care.

As illustrated in FIG. 1, a patient-centric workflow has three major elements: welcoming 10, caring 12, and aftercare 14. However, understanding and applying patient-centric workflow is not enough.

Physicians are knowledge workers whose activities blend cognitive, interpersonal and physical activities to serve patients. Their activities can be represented in a virtual, knowledge-oriented value chain for physicians. The "links" of the value chain are:

Data Gathering: Collecting patient and other data from histories, medical records, laboratory tests, diagnostic images, procedures and other sources.

Decision Making: Using the specific data collected above as well as background and researched knowledge from multiple sources to make diagnostic, therapeutic, prognostic and other medical, ethical, social and other decisions.

Distributing (Managing) Resources: Once the clinical decisions are made, the physician manages his own, the patient's and families' and the organization's resources to implement the diagnostic, therapeutic or other decisions.

eD-ucating: To appropriately implement the decision making, the physician interacts with the patient, family and various staff of the health care organization sharing knowledge.

Doing: Once resources are in place, the physician acts on her/his decisions to obtain the desired results.

Documenting: The results of the clinical activities are documented.

Figure 2:
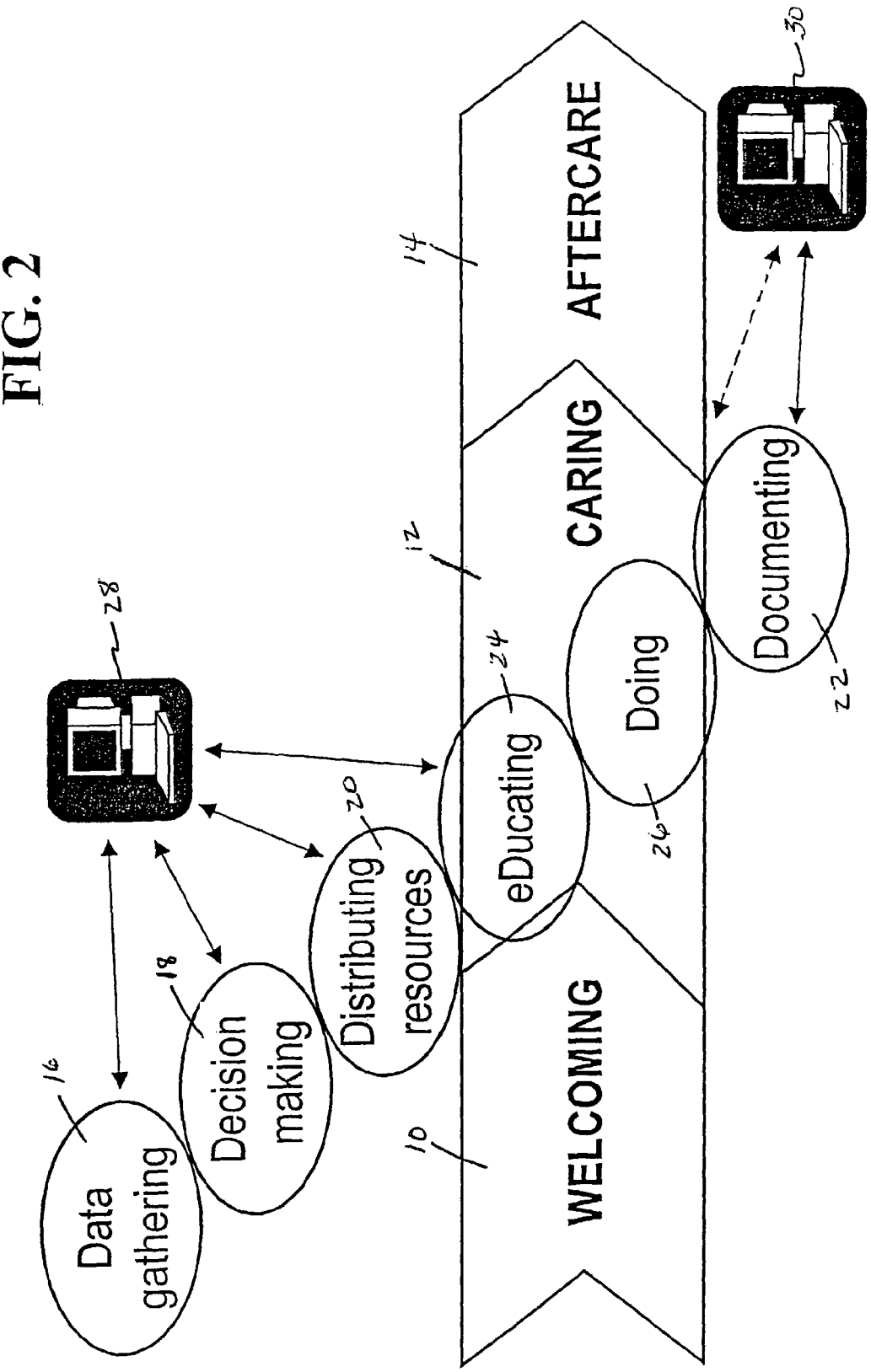
FIG. 2 shows a physician virtual value chain superimposed on the diagram of FIG. 1.

The physicians' value chain is illustrated by the diagonal "links" of FIG. 2.

Four of these elements: Data Gathering 16, Decision Making 18, Distributing Resources 20 and Documenting 22 can be done anywhere. The physician does not have to be at the health care organization to accomplish these if s/he has access to information and information systems linked to the organization. Hence, these are virtual activities. As illustrated in FIG. 2, the major intersection of the health care organization's patient-centric physical workflow and the physician's virtual value chain are eD-ucating 24 and Doing 26. Only the element of Doing has to be done on site, while eD-ucating (i.e., educating) would frequently be done on site.

As indicated by computer icons 28 and 30, information technology systems can enhance Data Gathering, Decision Making, Distributing Resources and Documenting by allowing the physician to accomplish these quickly, at her/his convenience anyplace and anytime thereby enhancing her/his productivity. Also, the automation of these steps can enhance quality and safety by including internal checks for consistency (checking for drug allergies or interactions) as well as providing decision assistance tools such as electronic medical references. It is unlikely that information technology by itself will help physicians' productivity in Doing as much as advances in biomedical technology and information technology embedded in biomedical technology. However, information technology may be helpful in assisting physicians in eD-ucating by providing educational material for patients, families and staff.

Prior to attempting to implement CPOE in automating the step of Distributing Resources, value can be added to physicians' work by making it easier and quicker for them (that is, decreasing their transaction costs), and by enhancing the quality of decision making and safety by addressing the elements of the virtual value chain in the following order:

Make it easier to gather clinical information, i.e., not waste time tracking down the chart, labs, x-rays, etc. (Data Gathering);

Provide passive decision assistance tools, that is, easily searchable electronic references (Decision Making);

Continue to enhance the documentation process, e.g. ease and speed of transcription (Documenting); Provide tools for patient education especially about medical procedures, hospital processes, expectations and recovery, etc. (eD-ucating); and Address CPOE by physician order entry or clinical order entry by a member of the health care team (Distributing Resources).

From a Patient-Centric Process perspective, the activities of the health care organization are defined by the various ways in which patients interact with the health care organization. Patient-Centric Processes include, for example:

Information Request: An individual contacts the health care organization in person, by phone or by computer to obtain information.

Ambulatory Test: An individual comes to a facility for a scheduled or unscheduled outpatient test.

Ambulatory Procedure: An individual comes to a health care facility for a scheduled physician procedure.

Non-urgent Ambulatory Visit: An individual comes to a health care facility for scheduled or unscheduled non-urgent evaluation and treatment.

Urgent Ambulatory Visit: An individual comes to a health care facility for an unscheduled urgent evaluation and treatment.

Urgent non-ambulatory visit: An individual is brought to a health care facility for an unscheduled urgent evaluation and treatment.

Elective Medical Admission: An individual comes to a health care facility for a scheduled medical (non-surgical) admission.

Elective Surgical Admission: An individual comes to a health care facility for a scheduled surgical procedure.

Urgent Medical Transfer: An individual is transferred urgently from another health care facility for a medical (non-surgical) admission.

Urgent Surgical Transfer: An individual is transferred urgently from another health care facility for a surgical procedure.

Critical Care: An individual requires an intensive level of medical care.

Long-Term Care: An individual is admitted to a facility for long-term care.

Home Care: An individual receives a health care worker into her/his home for medical care.

Each of these Patient-Centric Processes may be viewed as having three sets of activities:

Welcoming: Preparing for and welcoming the individual to the health care environment, understanding who s/he is and her/his needs and reason for the visit.

Care: Providing care for the individual's needs.

Aftercare: Providing support for the individual after the care is provided as well as handling the recuperation, administrative and financial aspects of the care delivery.

These activities are illustrated in the diagram of FIG. 1.

Each of the Patient-Centric Processes has physical aspects and virtual or information aspects. Each can be described in the "physical world of resources," the physical value chain from the patient's perspective, and the "virtual world of information," the virtual value chain of information needed for the health care organization and the "links" of the physicians' value chain discussed above. As noted in the Virtual Value Chain article noted above, this approach allows executives to "pay attention to how their companies create value in both the physical world and the virtual world."

Health care organizations are very complex organizations, which owe their success to the activities of many players. In order to gain a better understanding of their activities, health care organizations must understand how their major functional areas interact with the physical Patient-Centric Processes and how the virtual value chains of information flow. The major functional areas include:

Governance: Responsible for strategic management of the organization.

Medical Staff: Primary responsibility for patient care.

Nursing: Major party for delivery of health care services of the organization.

Ancillary Services: Assist in diagnosis and treatment, such as x-ray.

Administration: Manage admissions, billing and administrative processes.

Operations: Responsible for facilities, equipment, food and support services.

Financial: Manages the financial aspects of the organization.

Shared service/infrastructure: Information technology, human resources, etc.

Other.

Each of these areas must define their role in each of the Patient-Centric Processes in the physical workflow of the physical value chain, as well as in the information flow of the virtual value chain.

A key knowledge worker of this group is the physician, who may not be an employee and who plays a special role in managing the health care organization's resources. It is due to this special role that a unique virtual value chain is defined for the physicians, while the other players' roles are integrated in the organization's physical and virtual value chain.

FIG. 2 shows a physician virtual value chain superimposed on the diagram of FIG. 1. As indicated by FIG. 2, the physician virtual value chain and the patient-centric workflow "intersect" at workflow element 12, caring. In that element, the physician may spend time educating a patient, and in performing procedures, conducting examinations, and doing other tasks to render the appropriate care. In these instances, the patient and physician must generally be in the same physical location at the same time. It is noted that technology is developing exceptions to this requirement. For instance, robotic surgery maybe performed in which a physician may be remotely located from the patient. However, both patient and physician must be in a specific location, with one interacting with the other, in such cases. For purposes of this invention, such cases are considered to require the presence of both patient and physician, and thus would represent an instance in which the physician's value chain and the patient-centric workflow intersect.

FIG. 3 is a flowchart key used in connection with interpreting the flowcharts of the remaining figures. The symbols in FIG. 3 represent 5 categories of healthcare personnel, by columns, as follows: physicians 32, nurses 34, clerks 36, other 38 and other ancillary 40. The icons further represent 3 classifications of tasks, by rows, as follows: physical 42, virtual 44, and both physical and virtual 46. The other icons in FIG. 3 represent decisions to be made (icon 48) and activities or documents not associated with an individual (at icon 50).

Figure 4A:
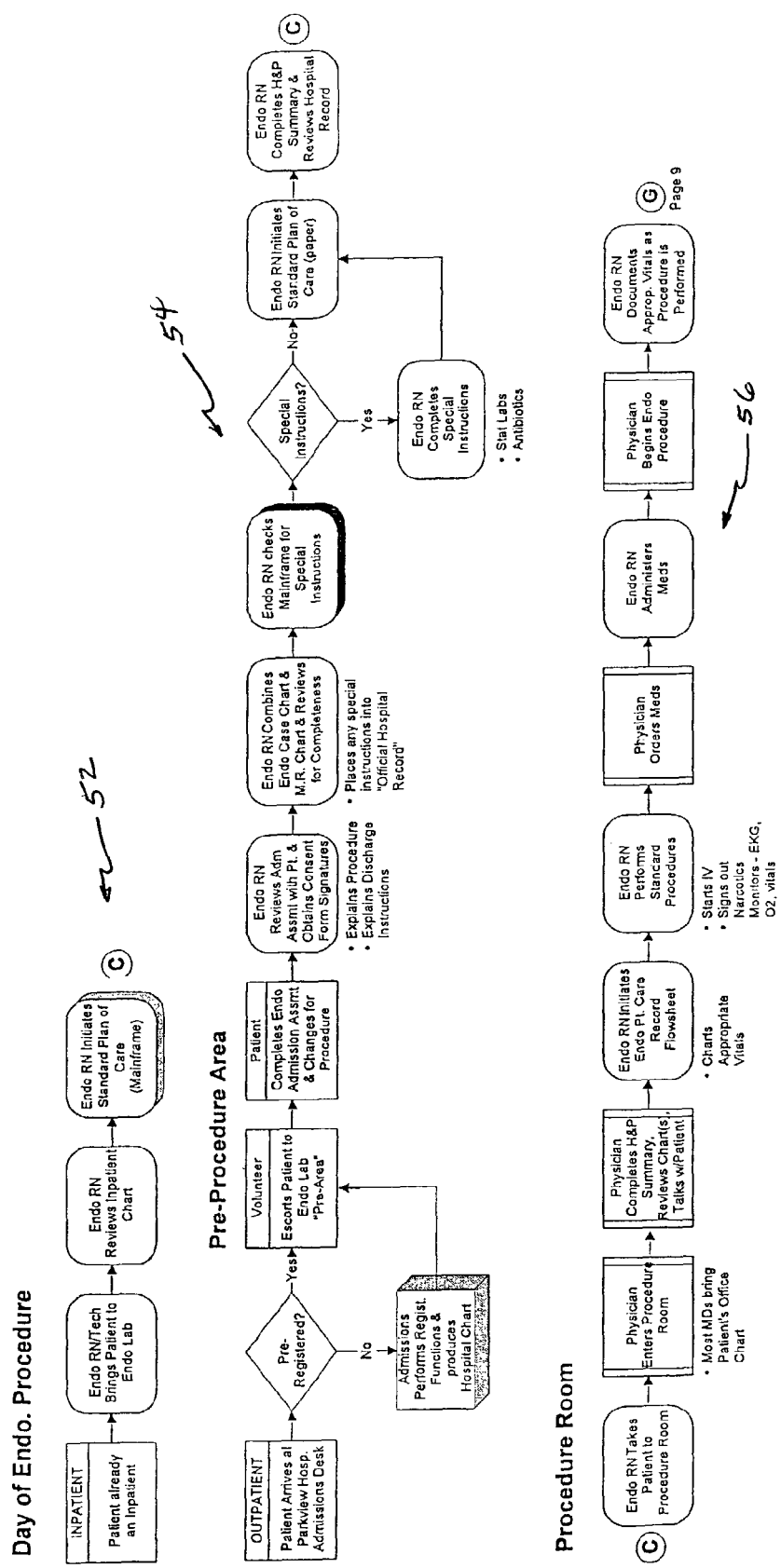
FIG. 4a is a diagram which illustrates a portion of an endoscopic procedure workflow.
Figure 4B:
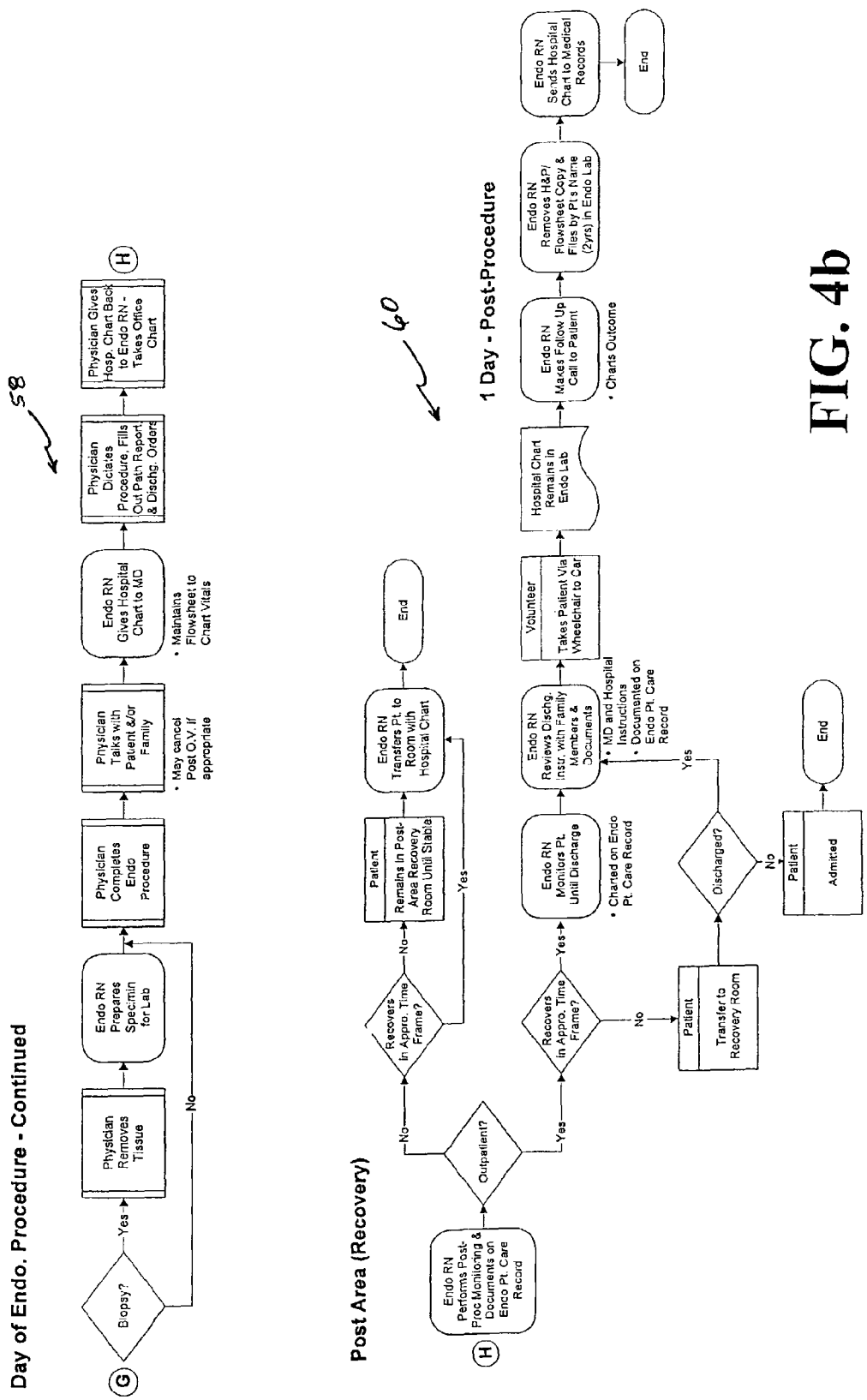

FIGS. 4a and 4b illustrate one embodiment of a portion of a patient-centric workflow for an endoscopic procedure. The flowpath indicated by reference numeral 52 is specific to an inpatient endoscopic procedure in an ambulatory environment. The flowpath indicated generally by reference numeral 54 is specific to a procedure performed on an outpatient basis. The workflow generally indicated by reference numeral 56 in FIG. 4a, and by reference numerals 58 and 60 of FIG. 4b, are common to both inpatient and outpatient procedures.

As indicated, the workflow diagrams of FIGS. 4a and 4b represent a portion of the tasks or steps performed in one embodiment of an endoscopic procedure. The entire procedure, of which the portions depicted in FIGS. 4a and 4b are a part, can be depicted in approximately 124 steps or tasks. Of these tasks, approximately 85% can be classified as physical tasks, approximately 10% can be classified as virtual tasks, and approximately 5% can be classified as combined physical/virtual tasks.

Figure 5A:
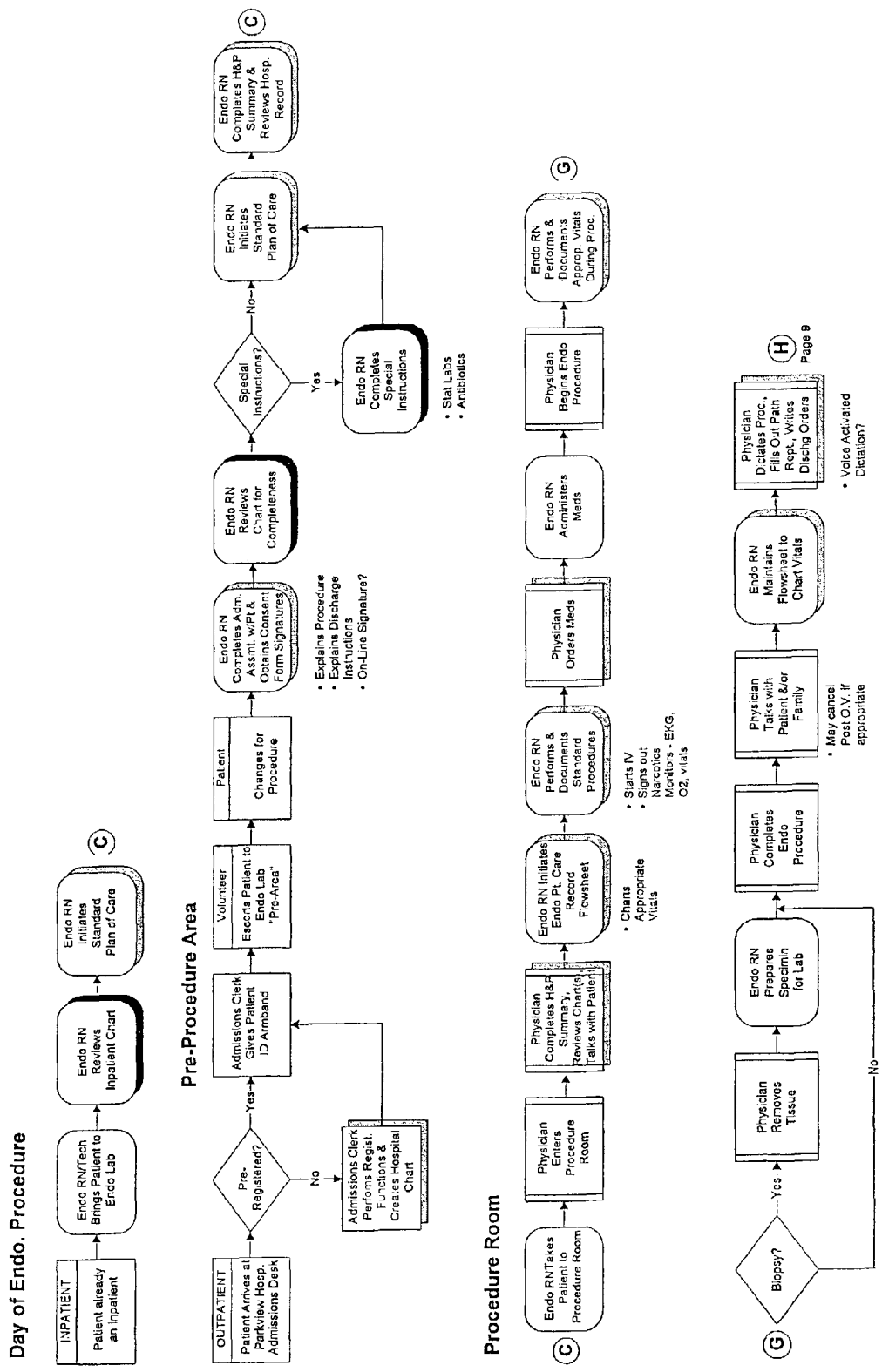
FIG. 5a is a diagram which illustrates a portion of an alternative endoscopic procedure workflow.
Figure 5B:
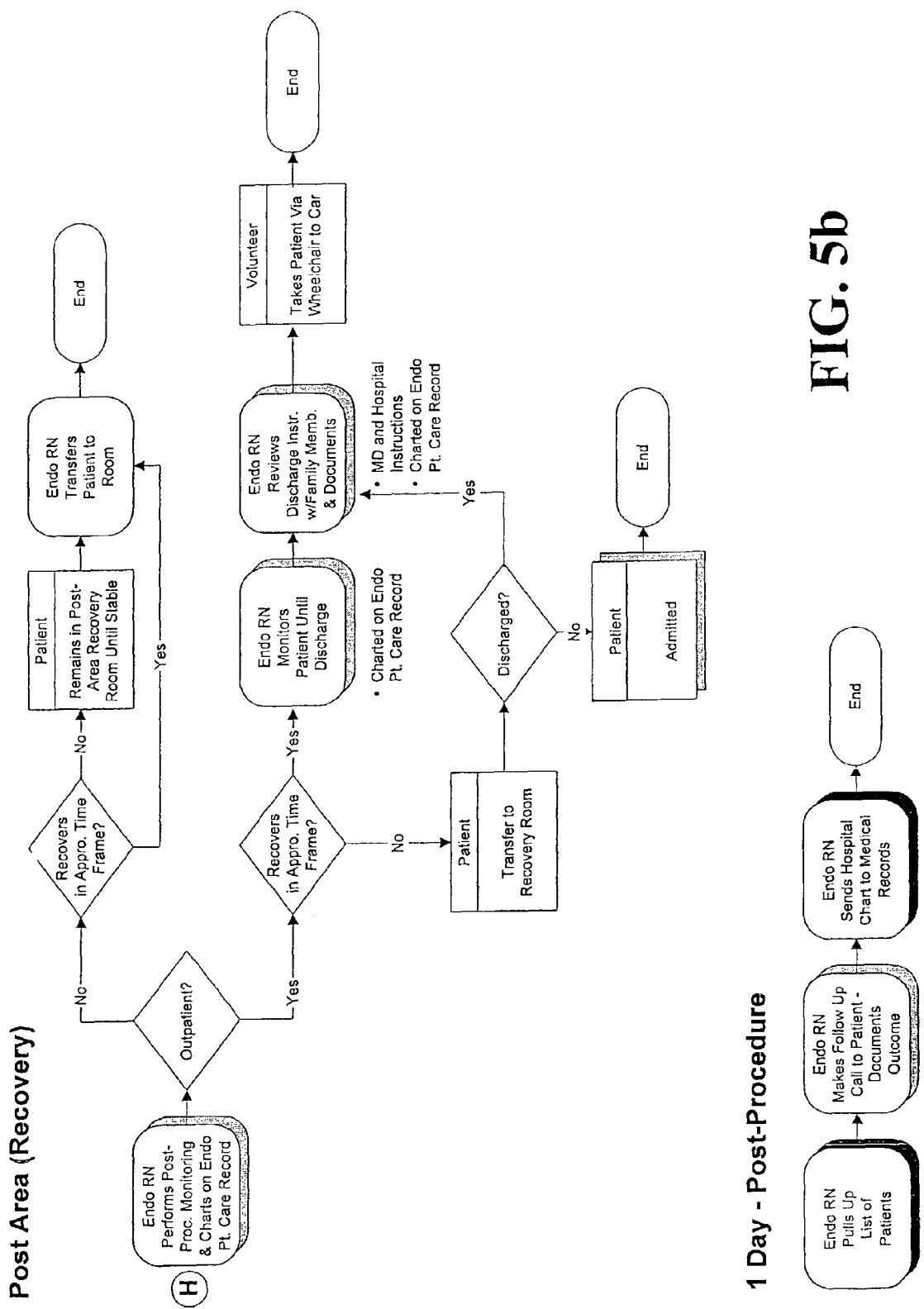

FIGS. 5a and 5b illustrate a portion of an alternative endoscopic procedure workflow. The portion of the alternative procedure illustrated in FIGS. 5a and 5b represents the same corresponding portion as is illustrated by FIGS. 4a and 4b. The entire procedure, of which FIGS. 5a and 5b represent a portion thereof, can be illustrated in approximately 118 steps or tasks. Of these, approximately 30% are classified as physical tasks, approximately 42% are virtual tasks, and approximately 28% are combined physical/virtual tasks. Due to the reduction in the number of tasks and the increased percentage of the tasks that are at least virtual tasks in part, the procedure associated with FIGS. 5a and 5b is considered to be advantageous to the physician, the patient and the healthcare organization.

Figure 6:
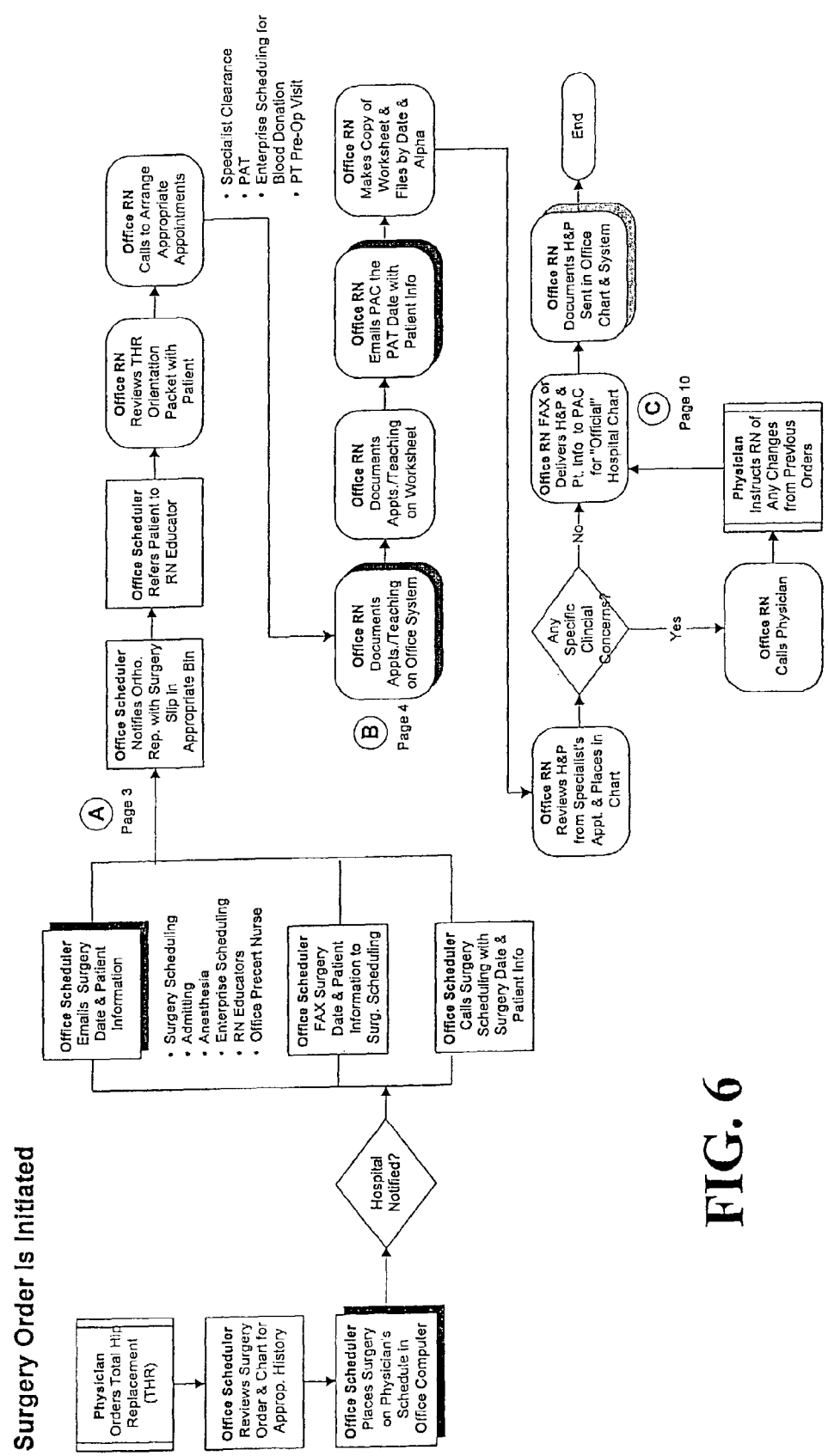
FIG. 6 is a diagram which illustrates a portion of a total hip replacement procedure workflow.

FIG. 6 is a workflow diagram which illustrates a portion of a total hip replacement procedure workflow. As is the case with the endoscopic procedure discussed above, the workflow diagram of FIG. 6 represents only a portion of an embodiment of a hip replacement procedure. The entire procedure may be represented by approximately 290 steps or tasks. Of these, approximately 84% may be classified as physical tasks, approximately 13% as virtual tasks, and approximately 3% as combined physical/virtual tasks.

Figure 7:
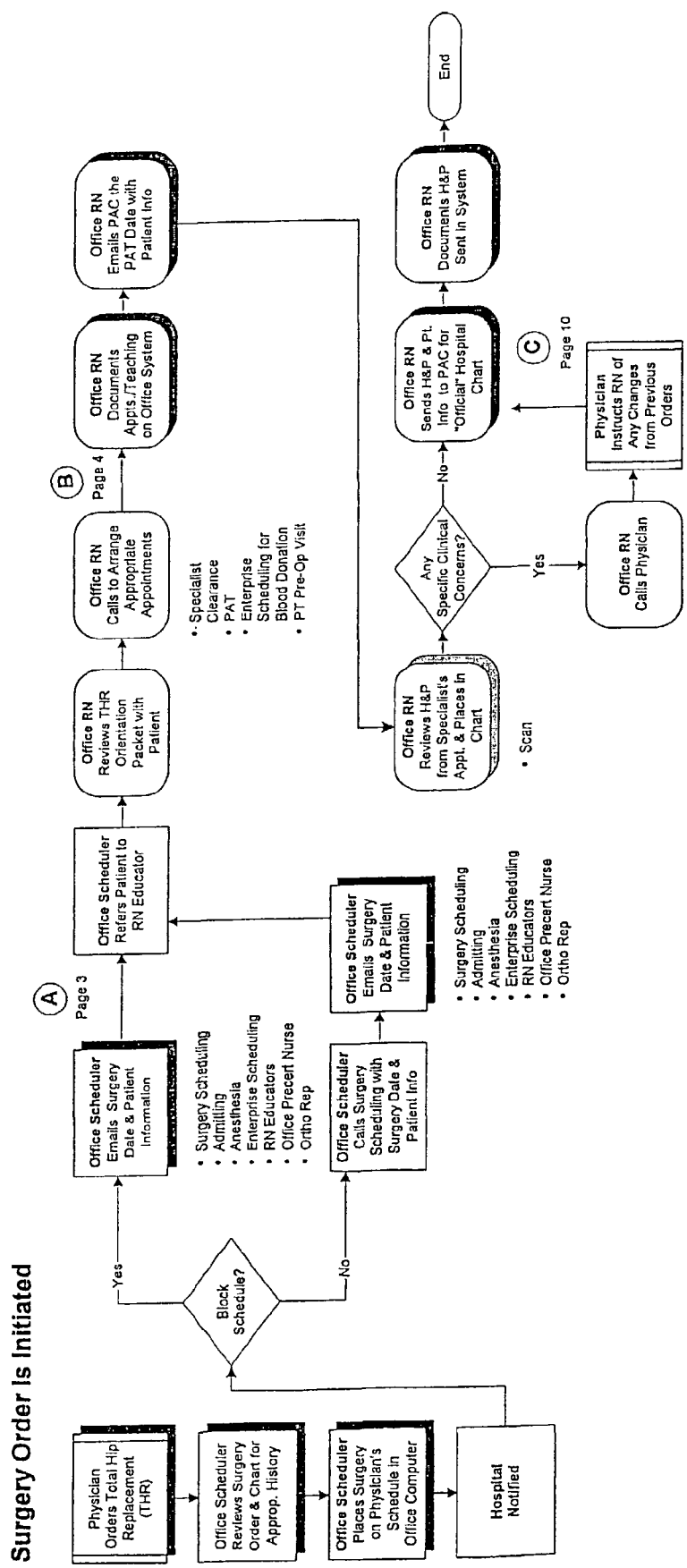
FIG. 7 is a diagram which illustrates a portion of an alternative total hip replacement procedure workflow.

FIG. 7 is a workflow diagram which illustrates a portion of an alternative total hip replacement procedure workflow. The diagram of FIG. 7 represents the same portion of the alternative procedure as that illustrated by FIG. 6. The entire alternative procedure, of which FIG. 7 illustrates a portion, may be completely illustrated by approximately 242 tasks. Of these, approximately 40% are physical tasks, approximately 41% are virtual tasks, and approximately 19% are combined physical/virtual tasks.

Figure 8:
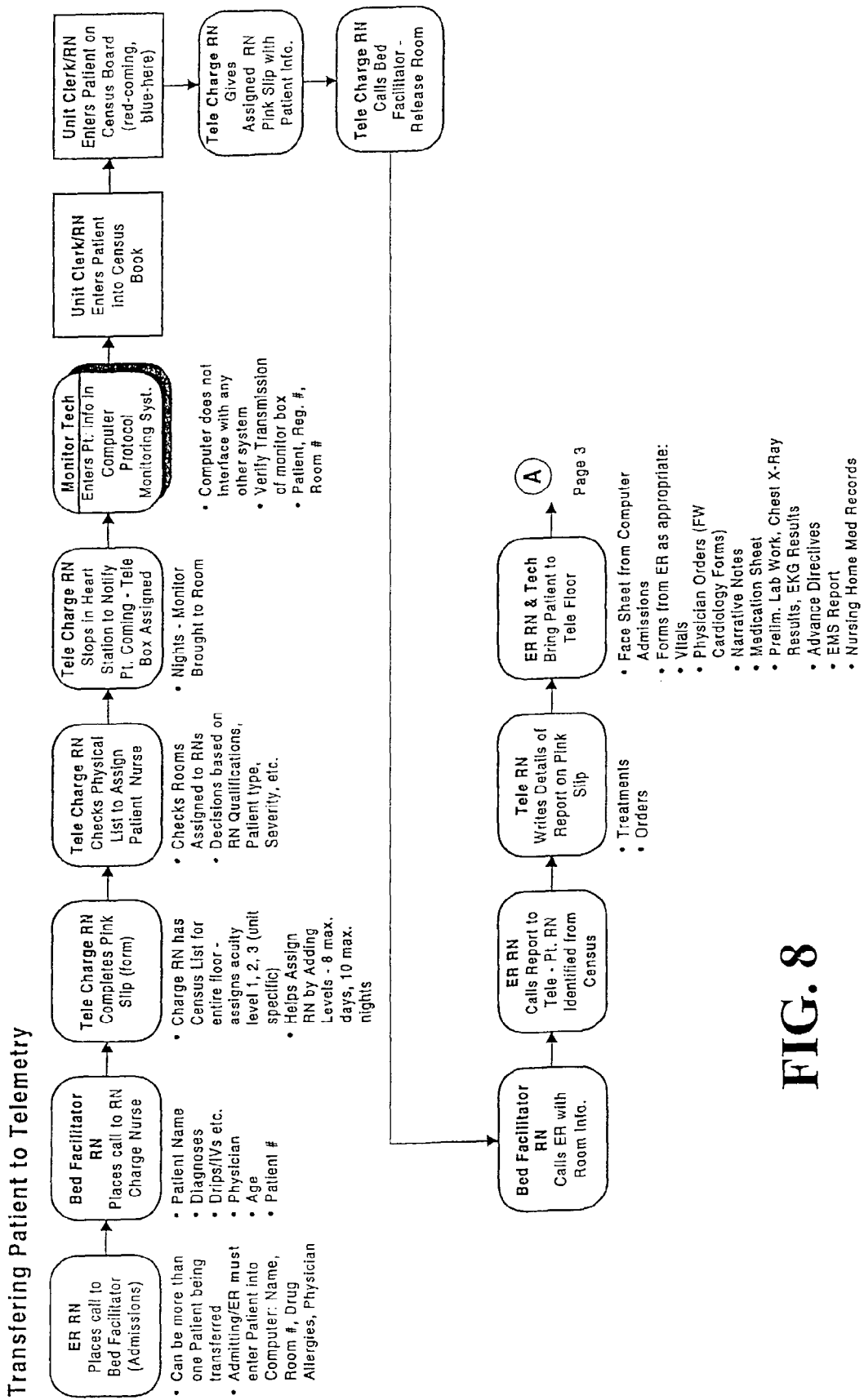
FIG. 8 is a diagram which illustrates a portion of a cardiac intensive care unit procedure workflow.

FIG. 8 is a workflow diagram which illustrates a portion of a cardiac intensive care unit procedure workflow. As is also the case with the endoscopic and total hip replacement procedures described above, the workflow diagram of FIG. 8 represents only a portion of an embodiment of a cardiac intensive care unit procedure. The entire procedure may be represented by approximately 349 tasks. Of these, approximately 83% may be classified as physical tasks, approximately 15% as virtual tasks, and approximately 2% as combined physical/virtual tasks.

Figure 9:
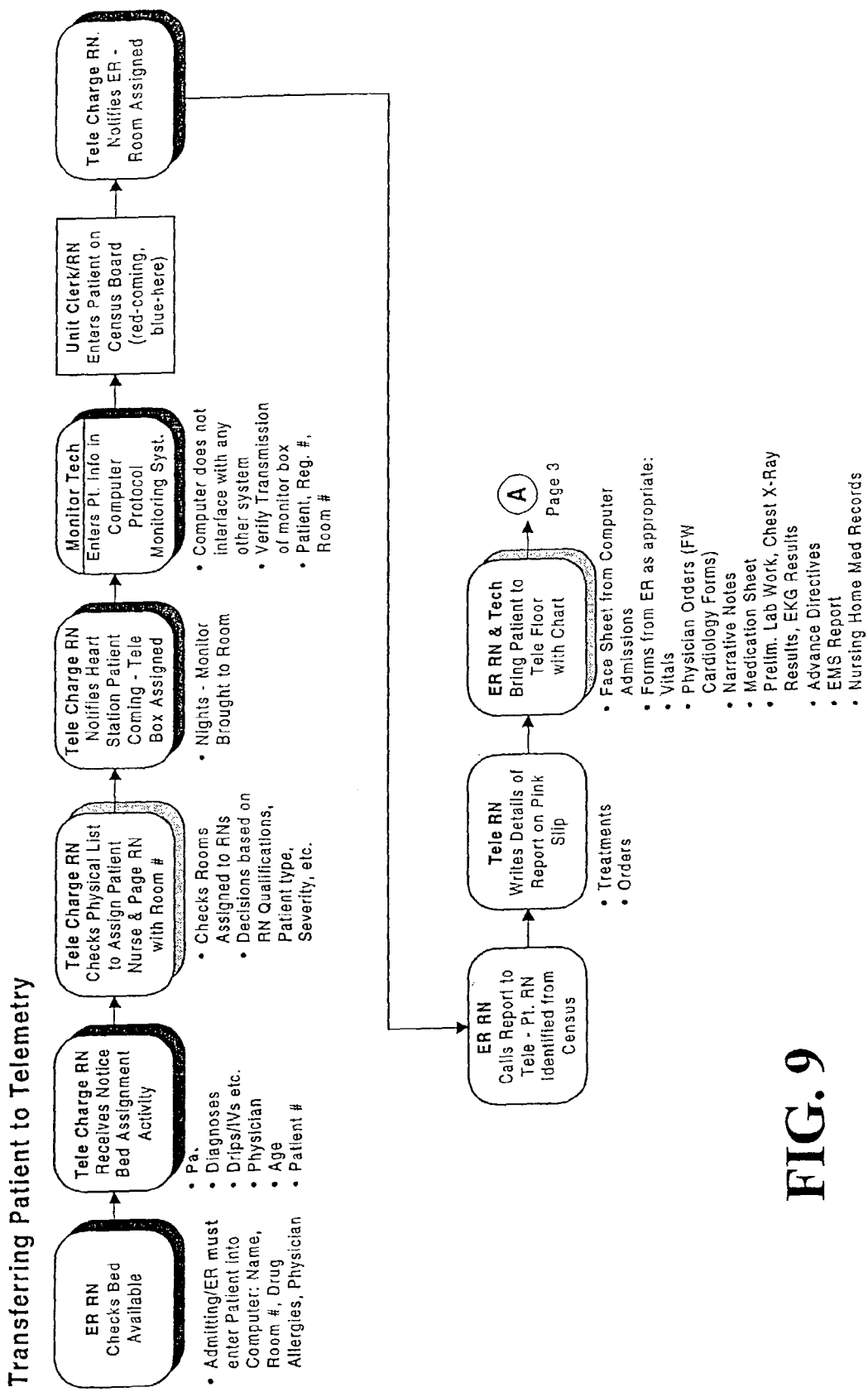
FIG. 9 is a diagram which illustrates a portion of an alternative cardiac intensive care unit procedure workflow.

FIG. 9 is a diagram which illustrates a portion of an alternative cardiac intensive care unit procedure workflow. The diagram of FIG. 9 represents the same portion of the alternative procedure as that illustrated by FIG. 8. The entire alternative procedure of which FIG. 9 illustrates a portion, may be completely illustrated by approximately 331 tasks. Of these, approximately 56% may be classified as physical tasks, approximately 3% as virtual tasks, and approximately 21% as combined physical/virtual tasks.

The present invention is intended to be implemented in the context of currently available computing technology. Such technology includes a processor or processors, storage devices, display devices, input and output devices, communication devices, and other well-known peripherals. Processing may be accomplished by using a central processing unit (CPU), or through distributed processing, or by a combination of same. It is likely that a local or wide area network will be employed in implementation.

Storage devices which may be used with the present invention include conventional magnetic and optical storage techniques, as well as techniques which may be developed to replace or enhance these conventional technologies. The practice of the present invention may be consistent with, but is not dependent upon the development of, future technological developments in the field of information processing.

Although the above description refers to particular means, materials and embodiments, one skilled in the art can easily ascertain the essential characteristics of the present invention. Various changes and modifications may be made to adapt to various uses and characteristics without departing from the spirit and scope of the present invention as set forth in the following claims.

What is claimed is:

1. A computer-implemented method of administering the delivery of health care services, comprising the steps of:
   a) providing a computer having a processor and a storage device;
   b) identifying a patient-centric process which forms at least a portion of a health care service and storing data relating to said process in the storage device;
   c) identifying a plurality of tasks associated with said process and storing data relating to said tasks in the storage device;
   d) using the computer:
      1. classifying said tasks as one of a physical task, a virtual task and a combined physical and virtual task; and
      2. further classifying said tasks as one of a physician-performed task and a non-physician-performed task;
   e) using the processor and the stored data relating to the classified tasks, producing a process workflow which incorporates the classified tasks, wherein said step of producing a process workflow comprises the steps of using the processor to create a flow diagram for at least a portion of said health care delivery process, and identifying at least a portion of a plurality of tasks defined in the flow diagram as one of a physical task, a virtual task and a combined physical/virtual task; and
   f) redesigning said process, using said process workflow created using the processor, to include an alternative set of patient-centric tasks so as to enhance efficiency of the process and productivity of the physician, whereby said process is changed by reducing the number of physical tasks relative to the number of total tasks or the number of virtual tasks in said process workflow.

2. The computer-implemented method of claim 1, further comprising the additional step of providing means for remotely performing a plurality of the physician-performed tasks classified as virtual and combined physical/virtual tasks.

3. The computer-implemented method of claim 1, further comprising the additional step of providing automated means for facilitating at least one of a physician-performed task relating to one of data gathering, decision making, distributing resources, educating, doing and documenting.

4. The computer-implemented method of claim 1, further comprising the step of identifying functional areas of one or more health care organizations responsible for at least one of said plurality of tasks.

5. The computer-implemented method of claim 1, further comprising the additional step of providing means for remotely performing a plurality of the nonphysician-performed tasks classified as virtual and combined physical/virtual tasks.

6. The computer-implemented method of claim 1, further comprising the additional step of providing automated means for facilitating at least one of a nonphysician-performed task relating to one of data gathering, decision making, distributing resources, educating, doing and documenting.

\* \* \* \* \*